(12) United States Patent
Fang et al.

(10) Patent No.: US 8,293,484 B2
(45) Date of Patent: Oct. 23, 2012

(54) METHOD AND DEVICE FOR PROTEIN DELIVERY INTO CELLS

(75) Inventors: Ye Fang, Painted Post, NY (US); Fang Lai, Painted Post, NY (US); Laurent A. G. Picard, Corning, NY (US); Brian L. Webb, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 99 days.

(21) Appl. No.: 12/893,389

(22) Filed: Sep. 29, 2010

(65) Prior Publication Data
US 2012/0083428 A1    Apr. 5, 2012

Related U.S. Application Data

(62) Division of application No. 11/261,198, filed on Oct. 27, 2005, now Pat. No. 7,829,290, which is a division of application No. 10/208,894, filed on Jul. 30, 2002, now Pat. No. 7,105,347.

(51) Int. Cl.
*G01N 33/53* (2006.01)
(52) U.S. Cl. .................................. 435/7.1; 436/518
(58) Field of Classification Search .................. None
See application file for complete search history.

(56) References Cited

U.S. PATENT DOCUMENTS

| | | | |
|---|---|---|---|
| 5,512,474 A | 4/1996 | Clapper et al. | 435/402 |
| 5,547,841 A | 8/1996 | Marotta et al. | 435/6 |
| 5,601,980 A | 2/1997 | Gordon et al. | |
| 5,731,152 A | 3/1998 | Maracas et al. | |
| 5,807,522 A | 9/1998 | Brown et al. | |
| 6,544,790 B1 | 4/2003 | Sabatini | 435/455 |
| 6,632,928 B1 | 10/2003 | Neville et al. | 530/388.75 |
| 6,777,239 B2 * | 8/2004 | Dower et al. | 436/6 |
| 2002/0137059 A1 | 9/2002 | Wu et al. | 435/6 |
| 2003/0124029 A1 | 7/2003 | Webb et al. | 422/102 |
| 2004/0146944 A1 | 7/2004 | Fang et al. | 435/7.2 |
| 2004/0241751 A1 * | 12/2004 | Wagner et al. | 435/7.1 |

FOREIGN PATENT DOCUMENTS

| | | |
|---|---|---|
| WO | WO 00/16893 | 3/2000 |
| WO | WO 00/63419 | 10/2000 |
| WO | WO 01/20015 | 3/2001 |
| WO | WO 02/14860 | 2/2002 |
| WO | WO 02/37944 | 5/2002 |
| WO | WO 03/076588 | 9/2003 |

OTHER PUBLICATIONS

Daniel D. Clark et al., "Rapid Detection of Protein Tyrosine Kinase Activity in Recombinant Yeast Expressing a Universal Substrate", Journal of Proteome Research, 2002, vol. 1(3).
Joanne D. Andreadis et al., "Use of Immobilized PCR Primers to Generate Covalently Immobilized DNAs for In Vitro Transcription/Translation Reactions", Nucleic Acids Research, 2000, vol. 28, No. 2, pp. i-viii.
Mingyue He et al., Single Step Generation of Protein Arrays from DNA by Cell-Free Expression and In Situ Immobilisation (PISA method), Nucleic Acids Research, 2001, vol. 29, No. 15, pp. 1-6.
Junaid Ziauddin et al., "Microarrays of Cells Expressing Defined cDNAs", Nature, vol. 411, May 3, 2001, pp. 107-110.
Stephen L. Hussey et al., "Efficient Delivery of Streptavidin to Mammalian Cells: Clathrin-Mediated Endocytosis Regulated by a Synthetic Ligand", Journal of Am. Chem. Soc. 2002, vol. 124, pp. 6265-6273.
Olivier Zelphati et al., "Intracellular Delivery of Proteins with a New Lipid-Mediated Delivery System", The Journal of Biological Chemistry, vol. 276, No. 37, Sep. 14, 2001, pp. 35103-35110.
A. Lalvani et al., "Rapid Effector Function in CD8+Memory T Cells", J. Exp. Med., vol. 186, No. 6, Sep. 15, 1997, pp. 859-865.
Alberts et al., Molecular Biology of the Cell, 3rd Edition, Eds, Garland Publishing, 1994, p. 22.
D. Derossi et al., "Trojan Peptides: The Penetratin System for Intracellular Delivery", Cell Biology, vol. 8, Feb. 1998, pp. 84-87.
S. Goldbard, "Simultaneous Interrogation of Multiple Receptors by Non-Positional Cell Arrays", Virtual Arrays, Inc., presentation at the Cell-Based Microarrays & High Content Screening, Mar. 20, 2002, San Diego, CA.
H. Härmä et al., "Miniature Single-Particle Immunoassay for Prostate-specific Antigen in Serum Using Recombinant Fab Fragments", *Clinical Chemistry*, 2000, vol. 46, No. 11, pp. 1755-1761.
Y. Kasuya et al., "Preparation of peptide-carrying microspheres with bioactivity on platelets", *J. Biomater. Sci. Polymer Edn.*, 1993, vol. 4, No. 4, pp. 369-380.
G. MacBeath et al., "Printing Proteins as Microarrays for High-Throughput Function Determination", Science, vol. 289, Sep. 8, 2000, pp. 1760-1763.
A. Scorilas et al., "Streptavidin-Polyvinylamine Conjugates Labeled with a Europium Chelate: Applications in Immunoassay, Immunohistochemistry, and Microarrays", *Clinical Chemistry*, 2000, vol. 46, No. 9, pp. 1450-1455.
S.R. Schwarze et al., "Protein transduction: unrestricted delivery into all cells?", *Trends in Cell Biology*, Jul. 2000, vol. 10, p. 209-295.
V. Väisänen et al., "Time-resolved Fluorescence imaging for quantitative histochemistry using lanthanide chelates in nanopart cles and conjugated to monoclonal antibodies", *Luminescence*, 2000, vol. 15, pp. 389-397.
Fox, Richard M., et al., "Incorporation of Deoxynucleotides into DNA by Diethylaminoethyldextran-Treated Lymphocytes", Biochemistry, vol. 16, No. 20, 1977.
Rigby, Perry G., "Prolongation of Survival of Tumour-bearing Animals by Transfer of "Immune" RNA with DEAE Dextran", Nature, vol. 221, p. 968-969, Mar. 9, 1969.

\* cited by examiner

*Primary Examiner* — Jacob Cheu
(74) *Attorney, Agent, or Firm* — Susan S. Wilks

(57) ABSTRACT

Methods for performing surface-mediated protein delivery into living cells, and fabricating protein-transfected cell cluster arrays are provided. The method comprises providing a protein-containing mixture; depositing said protein-containing mixture onto a surface at defined locations; affixing the protein-containing mixture to the surface as microspots; and plating cells onto the surface in sufficient density and under conditions for the proteins to be delivered into the cells. The protein-containing mixture comprises any suitable amino acid sequence, including peptides, proteins, protein-domains, antibodies, or protein-nucleic acid conjugates, etc., with a carrier reagent. Protein-transfected cell arrays may be used for rapid and direct, screening of protein or enzymatic functions or any given intracellular protein interaction in the natural environment of a living cell, as well as for high-throughput screening of other biological and chemical analytes, which affect the functions of these proteins.

22 Claims, 3 Drawing Sheets

METHOD AND DEVICE FOR PROTEIN DELIVERY INTO CELLS

CROSS-REFERENCE TO RELATED APPLICATIONS

This is a divisional of U.S. patent application Ser. No. 11/261,198 filed on Oct. 27, 2005, now U.S. Pat. No. 7,829,290, which is a divisional of U.S. patent application Ser. No. 10/208,894 filed on Jul. 30, 2002, now U.S. Pat. No. 7,105,347, the content of which is relied upon and incorporated herein by reference in its entirety, and the benefit of priority under 35 U.S.C. §120 is hereby claimed.

FIELD OF INVENTION

The present invention relates to biological arrays and assays. More particularly, the invention pertains to methods and devices for using surface-mediated protein delivery to transfect living cells.

SEQUENCE LISTING

This application contains a Sequence Listing electronically submitted via EFS-Web to the United States Patent and Trademark Office as pdf filed named "SP02-169B_seq_list_ST25.txt" having a size of 1 kb and created on Dec. 15, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

Genome sequencing projects have rapidly accelerated the pace of gene discovery and have led to the identification of thousands of new genes of higher order organisms, including humans. The challenge ahead is to identify the biological functions of many of the newly discovered genes. DNA microarray—also known as "gene-chip"—technology has emerged as a powerful tool for genome-wide analysis of gene expression and gene-sequence variations. One caveat of microarray technology is that protein abundance within the cell does not always correlate with expressed mRNA levels. Because the function of a gene is directly related to the activity of its translated protein, an alternative and possibly superior approach to elucidate gene functions lies in direct analysis of the functions of the specific proteins for which the gene encodes.

The current prevailing approach for analyzing protein function in vivo is to employ cell-based assays. These types of assays are used to study the function of one particular gene in a cellular context, through gene transfection and protein delivery. For the gene transfection approach, cells are transfected with a vector containing a specific gene that leads to the overexpression of the gene product. With regard to the protein delivery approach, cells are "transfected" with a functional protein, including antibodies, using membrane-disrupting, pore-forming reagents or other reagents, such as liposomes, as a carrier to deliver the protein across the cell membrane. Using a variety of functional assays, the effects of introduced DNA or proteins on cellular physiology are then detected.

Protein delivery, i.e., protein transduction is the process by which a peptide or protein motif crosses the cell plasma membrane. Traditionally, methods to introduce antibodies, peptides or other membrane-impermeable molecules into cells include micro-injection and electroporation. The obvious disadvantages of these techniques are that they tend to be toxic to the recipient cells, they are non-specific (i.e., anything can enter or exit the cell once the membrane is disrupted), and they exhibit low transfection efficiency and substantial variability. To overcome the disadvantage associated with these techniques, researchers have developed a number of protein-transduction domains (PTDs) that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. Recently, researchers have shown that a number of membrane-translocating peptides can successfully mediate delivery of polypeptides, protein domains, and full-length protein, including antibodies into cells using solution-based protein transfection protocols. Recently, researchers have also demonstrated the use of lipid liposomes or the like for protein delivery.

Traditionally, however, these approaches have been limited since they are solution-based formats. Only one gene or protein may be studied per assay. As more there are more than 35,000 genes present in the human genome, for instance, and approximately 10,000 of these genes are expressed as proteins in any given cell type, a high-throughput method for studying gene function is needed.

SUMMARY OF THE INVENTION

The present invention describes a strategy, which involves the creation of protein-transfection cell arrays or microarrays, for the high-throughput analysis of protein functions in prokaryotic and eukaryotic cells. Protein transfection cell arrays may be used for rapid and direct screening of protein or enzymatic functions or any given intracellular protein interaction in the natural environment of a living cell. Moreover, the protein transfection cell arrays also are useful for high-throughput screening of other biological and chemical analytes, such as drugs, which affect the functions of these proteins. The protein may include an intracellular protein, cell-surface protein, biologically active peptide, antibody, protein-nucleic acid conjugate, peptide-nucleic acid conjugate, fusion protein, synthetic peptide, protein-nanoparticle conjugate, protein-polymer conjugate, conjugate between a protein-organic chemical entity or protein-inorganic chemical entity, multi-protein complexes, or any amino-acid containing moiety.

The invention also discloses a method for transfecting living cells with proteins using surface-mediated delivery. According to an embodiment of the method, a substrate surface having a protein of interest or a protein to be introduced into cells, is used for culturing cells. The protein of interest or protein to be introduced into cells is pre-complexed with a carrier reagent before being applied to the surface. Cells are then overlaid onto the prepared surface. The carrier reagent promotes the delivery of the protein of interest into the cell, thus transfecting the cells. Alternatively, proteins of interest are attached on a suitable substrate surface, then a carrier reagent is added to the proteins to form complexes on the surface. In another embodiment, a fusion protein is used directly. The fusion protein contains a protein or a protein domain of interest, fused covalently with any kind of protein or peptide that exhibits properties for spontaneous intracellular penetration (e.g., a herpes simplex protein, VP22). Preferably, a mixture containing a protein of interest and a carrier reagent includes a helper reagent to enhance the protein delivery efficiencies. The present method produces a greater than 90% efficiency under optimized conditions for cell uptake of proteins. The present surface-mediated protein delivery technique is also referred to as a "reverse protein delivery."

The present invention also provides a method for fabricating an array of transfected cell clusters having a set of proteins of interest. The protein-transfection cell-cluster array can be used for functional screening or phenotype screening. One embodiment of the method comprises several steps. Provide a substrate with a surface. Provide a mixture solution containing a protein and a carrier reagent. Immerse the tip of a pin or other transfer device into the solution. Remove the tip of the pin from the solution with some of the solution adhering to the tip. Contact the substrate surface with the solution to transfer the solution from the pin tip to the surface. Repeat the contacting step a plurality of times to provide an array of protein microspots patterned on the surface. Deposit or plate cells, which are in an appropriate medium such as serum medium or serum-free medium, on top of the dried protein-containing microspots to allow reverse delivery to occur. In a variation of the method using a solution of a protein, the method further comprises incubating the protein microspots with a solution containing a carrier reagent, then plating cells on top of the dried protein-containing spots. The method can work also, mutatis mutandis, with a solution of a fusion protein that comprises a protein or a protein domain of interest and a carrier reagent (e.g., membrane-transducing peptides). A helper reagent may be also included in the complex formed by the protein and the carrier reagent, to enhance the protein delivery efficiencies. The helper reagent may be included in the solution containing the carrier reagent or more preferably, the helper reagent is pre-complexed with a protein before arrayed onto a surface. This method is referred to as a "living protein chip" or "living protein array" technology.

In an alternate embodiment, a protein array can be produced directly from DNA templates arrayed on a surface using cell-free protein synthesis. The arrayed DNAs would contain the coding regions of desired genes in addition to the regulatory regions required for transcription/translation and a tag moiety. Following conversion of the DNA array into protein using coupled transcription and translation, the produced proteins would be immobilized on the surface by means of the tag in an ordered array format. The proteins of the resulting protein array would be delivered into cells using a carrier or translocation peptide. The ability to generate arrays of cell clusters transfected with proteins synthesized directly from their corresponding DNA templates without having to purify the individual proteins a priori represents a significant advantage.

In another aspect, the present invention includes a cell array produced according to the present methods. A protein array having living cells comprises the use of a pre-patterned surface that contains non-cell adherent and cell-adherent areas. The protein mixture containing a protein of interest and a carrier reagent is deposited onto the cell-adherent area. Other surfaces, such as microcolumn or micropillar structures, may be also used for reverse protein delivery as described in U.S. patent application Ser. Nos. 09/962,054 and 10/155,098, incorporated herein by reference.

Other features and advantages of the present method and array device will become evident from the following detailed description. It is understood that both the foregoing general description and the following detailed description and examples are merely representative of the invention, and are intended to provide an overview for understanding the invention as claimed.

DETAILED DESCRIPTION OF THE INVENTION

Figure 1:
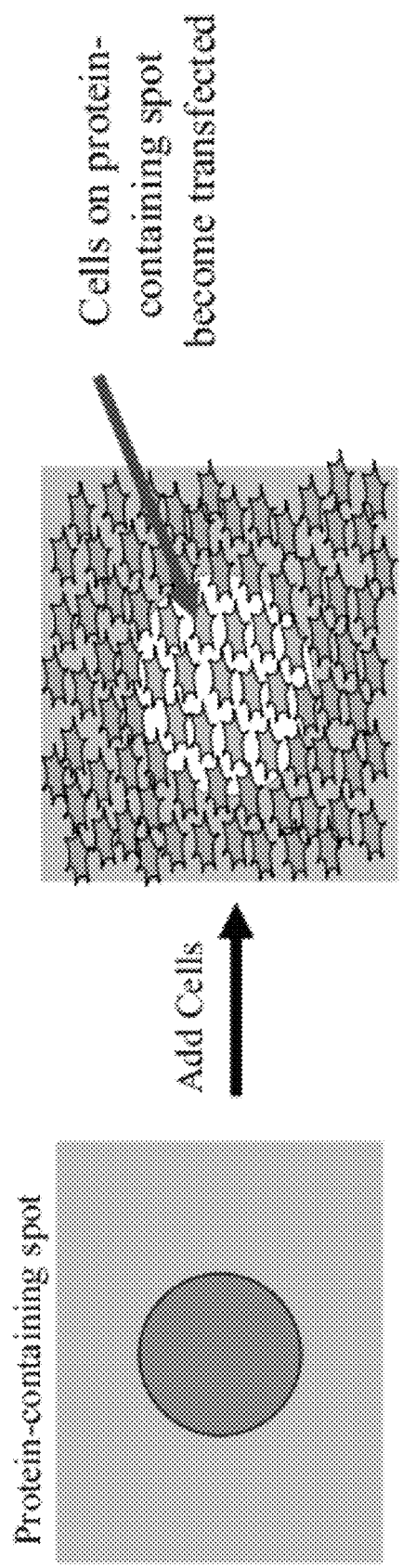
FIG. 1 depicts a schematic rendering of the present method to deliver proteins into living cells by a "reverse deliver" technique. A mixture containing: 1) a protein-of-interest, 2) protein-of-interest complexed with a carrier reagent, 3) a protein-of-interest-conjugate with a carrier reagent, or 4) a combination thereof, is deposited onto a surface (e.g., a glass slide, microcolumn, or the bottoms of wells in a multi-well plate) and dried to affix the proteins onto the surface. Cells are then desposited over the protein-containing spots, wherein the surface bearing the protein is used to culture the cells. Under appropriate conditions, the proteins enter and transfect the cells.

The present invention provides a surface-mediated, "reverse delivery" method of introducing proteins into living cells, in contrast to conventional techniques, wherein a cell culture is first provided followed by addition of a transfection solution containing proteins of interest to the cells. The present method affords researchers greater control over the exact sequence, content, amount and nature of the protein molecule. Not subject to the modifications and vagaries of relatively slow, in vivo protein synthesis, a researcher can pre-select, modify or check for uniformity of proteins prior to their introduction into cells. By varying the amount of protein on the surface, researchers can control the final intracellular protein concentration.

Recently, researchers have developed a microarray technique for expressing multiple genes in an array format using "reverse transfection." (Sabatini, D. & Ziauddin, J., "Microarrays of cells expressing defined cDNA," Nature 411, 107-110 (2001); International Patent Publication No. WO 01/20015, incorporated herein by reference.) According to their technique, a number of vectors, each containing specific sets of genes mixed with a carrier such as gelatin, are arrayed onto a surface, treated with transfection reagents, and overlaid with mammalian cells. After a relatively long period of time (>24 hrs.), the cells that attach to the surface become transfected. The cells overexpress the genes corresponding to the sample cDNA, producing an array of proteins in living cells, which can be used in gene functional studies. Unlike their technique, which is limited to gene encoding proteins, the present reverse protein delivery method can be used to deliver a broad range of proteins or protein-like biological molecules, including for example, functional peptides, antibodies, enzymes, particle-protein conjugates, and protein-complexes directly into a cell.

The present invention provides several advantageous and unique aspects, which differentiate it from other processes, including the reverse transfection method. A surface-mediated protein delivery to living cells is able to transfect multiple proteins in a single assay using the array format over traditional, solution-based cell protein delivery techniques. This virtue provides for simultaneous, parallel analysis of many different proteins for a desired cellular readout (e.g., apoptosis, changes in cell morphology, effects on signaling pathway, etc.). Such a high-throughput capability signifies that many more proteins can be screened per assay. The ability to screen more proteins per assay also reduces the amount of reagents consumed per assay, which can greatly reduce assay costs.

Delivery of proteins into cells has certain advantage over delivering DNA into cells by transfection. Since the protein molecule itself is being delivering into the cell and not the precursor gene, the present technique bypasses the transcription-translation process associated with gene expression. Hence, the protein will begin performing its biological functions immediately after entry into the cell, greatly shortening the duration of time until cells can be assayed for protein function. The shorter time period (<24 hrs.) required to manifest the effects of the delivered protein in the cell is due in part to an ability to bypass the transcription and translation process associated with gene expression. This feature is another advantage of the present method. Typically, one can see changes within 12 hours. In some cases, greater than 95% of proteins can be delivered in as little as 3-6 hours, or even as short as within 1 or 2 hours.

Another advantage of the method is that it can be used to assess the role of post-translational modification (PTM) on protein functions. Previously in DNA transfection methods, a protein would be modified after translation according to specific signals on the protein (e.g., glycosylation sites), which would be dependent on the availability of a correct set of enzymes in the target cell line. The present method circumvents this need to find a cell line that will perform these PTMs. Using an array of the present device, one can test the effect that different PTMs in a protein (e.g., various sugar groups), which have been engineered in vitro, have on the biological function of the protein in a cell, without need to mutate the DNA sequence, or alter the signals and/or transfect the DNA into an appropriate cell line.

Moreover, unlike gene transfection that is limited to only the expression of gene products, the present protein delivery approach can be used to transfect cells with a much broader range of biologicals, for instance, including bioactive peptides, proteins domains, proteins, antibodies, protein-nucleic acid conjugates, antibody-nucleic acid conjugates, nanoparticle-protein conjugates, multi-protein complexes, and any amino-acid containing moiety.

Furthermore, the method can make amenable studies of the same protein in different cells (e.g., a protein in differentiated and undifferentiated stem cells). For instance, even though certain mammalian cells are notoriously difficult to transfect, of the mammalian cell types tested to date according to the present invention, all were receptive to protein transduction (delivery). Another advantage of the present method is the ability to better control the biological effect by varying the dosage or quantity of protein per cell.

The invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In the present specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Reverse Protein Delivery

As FIG. 1 depicts in schematic drawings, the method comprises in its simplest form: depositing a protein-containing mixture onto a surface, and plating cells onto the surface in sufficient density and under appropriate conditions for delivering proteins in the protein-containing mixture into the cells. To illustrate, for example, mammalian cells are cultured on the mixture-coated surface. The cells take-up the protein(s), which may affect cellular functions or observable expression. A solution or mixture containing one or more kinds of proteins of interest may be deposited and affixed to the surface, and used for subsequent cell culture and transfection.

The protein-containing mixture comprises known or unknown protein(s) (e.g., cell extracts) and a carrier reagent. A protein of interest, or a protein to be introduced, may be a biologically active peptide, a protein domain, an intracellular protein, an enzyme, a cell-surface protein, a toxin, an antibody, an antibody-nucleic acid conjugate, a protein-nucleic acid conjugate, a peptide-nucleic acid conjugate, a fusion protein, a protein-nanoparticle conjugate, and a polymer. The surface bearing the protein-containing mixture can be used for culturing cells and, thereby, transfecting the adherent cells. The substrate used in the present invention can comprise various glass, silicon, metal or polymeric materials. The substrate can be configured as a bead, chip, slide, microwell plate, or a microcolumn device as described in co-assigned U.S. Provisional Application No. 60/317,660.

In an embodiment, the protein-containing mixture comprises protein and a carrier reagent that is present in an appropriate solvent, such as phosphate saline buffer. The protein is pre-complexed with the carrier reagent through physical interaction, for example, hydrophobic interaction or electrostatic interaction, etc. The mixture is spotted onto a surface, thus producing a surface bearing (having affixed thereto) the protein-containing mixture in a defined location. The resulting product is allowed to dry sufficiently, such that the spotted protein-containing mixture is affixed to the surface and the spots remain in the locations to which they become affixed, under the conditions used for carrying out subsequent steps in the method. Alternatively, the protein-containing mixture may further comprise a helper reagent. The helper reagent is included to increase the protein delivery efficiencies.

In another embodiment, a solution of a fusion protein is employed directly. The fusion protein comprises a conjugate of 2 parts: a protein or a protein domain of interest and a carrier sequence or reagent. The fusion protein solution is spotted onto a surface, thus producing a surface bearing (having affixed thereto) the fusion protein in a defined location. Again, the resulting product is allowed to dry sufficiently, such that the spotted protein-containing mixture is affixed to the surface and the spots remain in the locations to which they become affixed, under the conditions of use for subsequent steps in the method. Cells grown on the coated surface take up the protein, creating transfected adherent cells on top of the coated surface.

Alternatively, a mixture of fusion proteins (i.e., a protein or a protein domain and a carrier reagent) is complexed with a helper reagent. The mixture is spotted onto a surface, to produce a surface bearing (having affixed thereto) the fusion protein-containing mixture in a defined location. In a variation of the method, a solution of a protein is spotted onto a surface and allowed to dry sufficiently. A solution of a carrier reagent in the presence and absence of a helper reagent is applied to the protein-bearing surface to allow the protein on the surface to interact more easily with the reagents, thus promoting protein delivery into adherent cells occur.

In yet another embodiment of the method, a cell-free protein synthesis reaction can be performed, and the array of proteins produced is reacted with a vehicle reagent to transport the proteins into cells. Proteins are synthesized in situ on the coated surface of a substrate. Peptides or proteins immobilized on the surface are preferably produced using in vitro transcription/translation of DNA templates of particular genes, previously deposited on the surface. Since protein synthesis and purification is both cumbersome and time-consuming, especially for the large number of proteins warranted for array applications, the present method provides a simpler, faster method of producing and introducing proteins into cells. The DNA templates (representing full-length gene clones or gene fragments) can be produced either by PCR or RT-PCR using oligonucleotide primers. The templates would include a tag moiety, so that following conversion of the DNA into protein, using coupled transcription and translation, the tagged proteins would become immobilized on the surface. An example is a His-tag adhered to a Ni-NTA-coated surface. These proteins would be delivered into cells using a carrier or translocation peptide. Enzymatic-aided cleavage at a protein or protein cleavage site in the tag region, for instance, may be used to mediate the release of the synthesized proteins from the surface and entry into cells. Typical reagents used to perform this operation include glutathione-S-Transferase, thrombin and inteins. The inteins have the advantage of being autocatalytic; that is, another enzyme is not need to cleave off the protein of interest.

The production of the template DNAs can either be done prior to arraying using conventional PCR or RT-PCR, or the entire array of template DNAs can be synthesized on the substrate using solid-phase PCR by immobilizing one set of primers on the substrate surface. (See, Andreadis, J. D. and Chrisey, L. A., Nuc. Acids Research 28, 2, e5 (2000); He, M. and Taussig, M. J., Nuc. Acids Research 29, 15, e73 (2001); International Patent Application No. WO 02/14860 A1). The present cell-free, direct method of in situ protein synthesis obviates the need to produce and purify the hundreds or thousands of proteins of interest desired to transfect into cells. It also enables the transfection into cells of domains or parts of proteins using specific PCR primers designed to produce the desired product.

Protein Arrays with Living Cells

Figure 2:
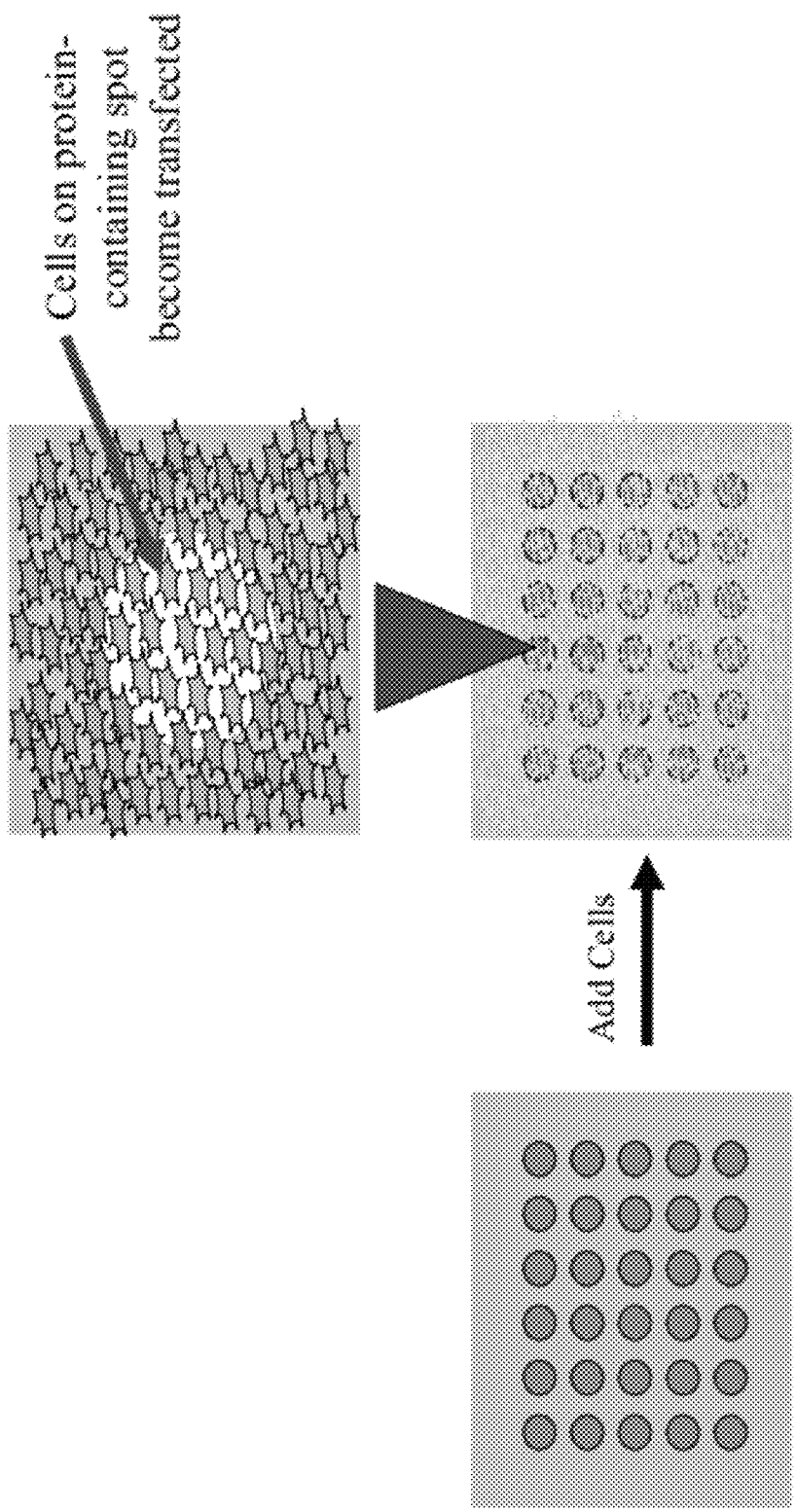
FIG. 2 depicts a schematic rendering of the present method to deliver proteins into living cells to form a transfected cell cluster array. A set of mixtures, containing a set of proteins of interest like in FIG. 1, were arrayed onto a surface in defined, discrete or distinct locations, and affixed to the surface. Cells plated and cultured over the surface bearing the proteins are transfected when the proteins are delivered into the cells, resulting in a transfected cell cluster array. A cell cluster array can be used in a variety of assays, such as for functional or phenotype screening.

As illustrated in FIG. 2, in an extension of the method, a solution or mixture containing a set of proteins of interest may be arrayed onto a surface in defined, distinct locations to create a rectilinear microarray or cluster array of cells with defined areas of adhered cells. Such microarrays may be employed in proteomic studies, such as functional or phenotype screening, or other high-throughput uses.

Depending on the desired use, living prokaryotic or eukaryotic cells (e.g., bacterial, mammalian, human, insect, or plant cells) may be plated in sufficient density onto the surface bearing the protein-containing mixture. The protein samples are pre-spotted in defined and discrete locations. Under appropriate conditions, the protein can be introduced into the cells. Preferably, the cells in an appropriate medium (either a serum or serum-free medium) are plated at high density on top of the dried protein-containing spots, so as to increase the likelihood that reverse delivery will occur. The protein presented in the protein-containing mixture affixed to the surface enters the cells. The resulting array of living cell clusters may be used to identify proteins that alter (enhance or inhibit) a pathway, such as a signaling pathway in a cell, or another property of a cell, such as its morphology.

As illustrated in FIG. 2, the array of the present invention includes a substrate having a surface with a plurality of protein-containing probe microspots. The microspots are affixed to the surface of a substrate. As used herein, the term "affixed" means that the microspots maintain their position relative to the substrate under both cell culture and transfection conditions. The means—covalent or electrostatic—by which a protein of interest adheres is not necessarily limiting of the invention. Cells that adhere to the top of each spot only uptake the proteins in the matrix arrayed on the surface to form a localized, transfected cell cluster array. Each probe microspot on the array may comprise a protein of either known or unknown composition. The protein preferably is pre-complexed with a carrier reagent in either the presence or absence of a helper reagent. Alternatively, the protein may be first arrayed onto a surface, then interacted with a carrier reagent or a fusion protein comprising a protein or a protein domain and a carrier reagent, in the presence or absence of a helper reagent.

The probe microspots on the array may have any convenient shape, but typically will be either circular, elliptoidal, oval, annular, or some other analogously rounded shape. The shape may, in certain embodiments, be a result of the particular method employed to produce the array, which is a non-limiting feature. The density of the microspots on the surface of the substrate (i.e., both probe spots and non-probe spots; e.g., calibration spots, control spots, etc.) generally does not exceed about $2000/cm^2$, but is at least $1/cm^2$ or $10/cm^2$ to about $60/cm^2$. In particular embodiments, the density does not exceed about $500/cm^2$, and in certain preferred embodiments, the density does not exceed about $400/cm^2$ or about $300/cm^2$. The microspots may be arranged generally in any convenient pattern over the surface of the solid or porous support. Typically, the pattern of spots will be present in the form of a grid, with rows and columns, across the surface of the substrate. The microspots, however, also may be arranged in a scatter or circular pattern, or the like.

In an embodiment of the array, each of the microspots of the array has a different protein. For instance, an array comprising about 100 microspots could comprise about 100 different proteins. Likewise, an array of about 10,000 microspots could comprise about 10,000 different proteins. The protein(s) included on one microspot differs from the protein(s) included on a second microspot of the same array. In such an embodiment, a plurality of different proteins is present on separate microspots of the array. An array may comprise at least about two different proteins, but more typically about 10 different proteins. More preferably, the array comprises about 50 to 100 different proteins. Most preferably, arrays may comprise about 1,000-15,000 or more different proteins.

In an alternative embodiment, each different protein is included on more than one separate microspot on the array. For instance, each different protein optionally may be present on two to six different microspots. An array of the invention, therefore, may comprise about 3,000 microspots, but only comprise 1,000 different proteins since each different protein is present on three different microspots. In a further alternative embodiment, each of the microspots of the array comprises the same protein of interest but with different point mutations. The resulting arrays can be used to systematically examine the structure and function relationship of the protein in cells.

Additionally, in yet another alternative embodiment, the array comprises substantially identical microspots (i.e., microspots comprising the same proteins) or a series of substantially identical microspots, which in use are treated with a chemical or biological moiety (e.g., drug or drug candidate). For example, an array of the invention can include a "mini array" of 10-20 or more microspots, each microspot containing a different protein, wherein the mini array is repeated 20 times as part of the larger array.

The protein of one microspot may be different from that of another, however, the proteins may be related. One microspot may comprise multiple, different proteins. For example, two different proteins involved in the same or similar signaling pathways can be included in one microspot. In a preferred embodiment, the two different proteins belong to a same signaling pathway. The different proteins on the invention array may be either functionally related or just suspected of being functionally related. Such designs can be used for thematic microarrays.

When the function of the proteins are unknown, the different proteins on the different microspots of the array may actually share a similarity in structure or sequence, or may be suspected of sharing a similarity in structure or sequence. Alternatively, the proteins may be fragments of different members of a protein family, or the proteins may share similarity in pharmacological and physiological distribution or roles.

Proteins

A variety of conventional means may be applied to produce the proteins used for reverse protein delivery in this invention. For instance, the protein may be obtained from natural sources or, optionally, be overexpressed using recombinant DNA methods. The protein may be either purified using conventional techniques or left unpurified. A large number of proteins are available commerically, and may be used in the present invention.

As mentioned previously, proteins may include intracellular proteins, cell surface proteins, toxin proteins, antibodies, synthetic peptides, bioactive peptides, and protein domains; also protein-nucleic acid conjugates, and protein-nanoparticle conjugates, or multi-protein complexes. Any other biologicals including nucleic acids and polymers are also included in this invention. Additionally, conjugates between a protein-organic chemical entity or protein-inorganic chemical entity (e.g., Biotin, fluorescent dies, silanol or silane derivatives, mass spectrometry tags, or low-molecular weight chemical moiety, etc.) are included.

Examples of intracellular proteins include, but are not limited to: oxidoreductases, transferases, hydrolases, lyases, isomerases, ligases, kinases, phosphoproteines, and mutator transposons, DNA or RNA associated proteins (for example, homeobox, HMG, PAX, histones, DNA repair, p53, RecA, robosomal proteins, etc.), electron transport proteins (for example, flavodoxins); adaptor proteins; initiator caspases, effector caspases, inflammatory caspases, cyclins, cyclin-dependent kinases, cytokeletal proteins, G-protein regulators, small G proteins, mitochondria-associated proteins, PDZ adaptor proteins, PI-4-kinases, etc. Recombinant proteins of unknown functions may also be used.

Applicable cell surface proteins include, but are not limited to: G-protein coupled receptors (e.g. the aderenergic receptor, angiotensin receptor, cholecystokinin receptor, muscarinic acetylcholine receptor, neurotensin receptor, galanin receptor, dopamine receptor, opioid receptor, erotonin receptor, somatostatin receptor, etc), G proteins, ion-channels (nicotinic acetylcholine receptor, sodium and potassium channels, etc), receptor tyrosine kinases (e.g. epidermal growth factor (EGF) receptor), immune receptors, integrins, and other membrane-bound proteins. Mutants or modifications of such proteins or protein functional domains or any recombinant forms of such proteins may also be used.

Toxin proteins include, but are not limited to, cholera toxin, tetanus toxin, shiga toxin, heat-labile toxin, botulinum toxin A & E, delta toxin, pertussis toxin, etc. Toxin domains or subunits may also be used.

Antibodies include, but are not limited to, organism-specific antibodies such as mouse and human antibodies, monoclonal and polyclonal antibodies, intact antibodies or single-chain antibodies.

Synthetic and bioactive peptides and protein domains also can be used to transfect cell using the method of the present invention. For example, a synthetic peptide comprising a sequence of AAYANAAVE may be used to transfect cells and monitor the protein tyrosine kinase (PTK) activity in cells. This peptide has recently been used as a universal PTK substrate for rapid detection of PTK activity in recombinant yeast (Clark, D. D. & Peterson, B. R., J. Am. Chem. Soc., 1, 207-209 (2002)).

Foreign proteins such as streptavidin and lectins and polymers may also be used.

Nanoparticle-protein conjugates may be used to transfect and visualize cells. The particles can include fluorescent tags, quantum dots, gold nanoparticles, paramagnetic nanoparticles, silica nanoparticles, or beads of silica glass or polymer material, or the like. In other embodiments, protein-DNA conjugates are used. The DNA is transcribed and translated into the resulting protein.

According to still another embodiment, the proteins may be synthesized in situ on the surface of the substrate. Since protein synthesis and purification of multiple proteins is both cumbersome and time-consuming, the present method provides a simpler, faster technique of producing and introducing proteins into cells. Coupled cell-free transcription/translation of DNA templates previously deposited on the surface produces the corresponding proteins immobilized on the surface. One can deposit an array of DNA templates on a substrate surface, perform in situ protein synthesis on the surface and then treat the resulting protein array with a vehicle reagent to transport the proteins into cells.

By spotting a library of fusion proteins on an appropriate substrate surface, and then plating adherent cell lines on the surface it is possible to assess the function of the protein in vivo in eukaryotic cells. Interactions between the delivered protein and other native cellular proteins may be studied in vivo. Fusing the delivered protein with an auto-fluorescent marker, such as the green fluorescence protein (GFP), may monitor intercellular localization of the delivered protein. Reverse delivery into cells could be accomplished, for instance, using VP22 fusion protein, herpes simplex protein, or any other protein with the similar properties. The fusion protein can be made using state-of-the-art methods. Some commercially available vectors for the production of VP22 fusion protein in mammalian cells and *Escherichia coli* (for example, pVP22/myc-His-2 from Invitrogen, Carlsbad, Calif.) are applicable. The fusion protein can be deposited directly and affixed onto the substrate surface, or the fusion protein can be pre-mixed with a helper reagent and then deposited and affixed onto the surface for transfecting cells.

Further, fusion-proteins are preferably deposited and affixed onto a number of distinct and defined locations, such as the bottom surface of wells in a microplate. In another embodiment, a library of fusion proteins to be introduced into cells are preferably deposited and affixed onto a number of defined and discrete locations of a surface to transfect cells. In one embodiment, the surface is a pre-patterned surface that contains non-cell adherent and cell-adherent areas. The fusion protein is deposited onto the cell-adherent area. In another embodiment, the fusion protein is deposited onto a number of defined and discrete locations in a surface, followed by treating the surface with a biological or a chemical to block these fusion protein-free surface areas from cell attachment.

Carrier Reagents

The particular embodiments of the invention are described in terms of a carrier reagent. Carrier reagents may comprise a variety of species. In one embodiment, the carrier reagent is a bioactive cell membrane-permeable reagent, or other peptides containing protein-transduction domains (PTDs) (i.e., single peptide sequences comprising about 15 to about 30 residues). Protein-transduction domains (PTDs) mediate protein secretion, and are composed of a positively charged amino terminus, a central hydrophobic core and a carboxyl-terminal cleavage site recognized by a single peptidase. Examples of such membrane-transducing peptides include Trojan peptides, human immuodeficiency virus (HIV)-1 transcriptional activator (TAT) protein or its functional domain peptides, and other peptides containing protein-transduction domains (PTDs) derived from translocation proteins such as Drosophilia homeotic transcription factor Antennapedia (Antp) and herpes simplex virus DNA-binding protein, VP22, and the like. Some commerically available peptides, for example, penetratin 1, Pep-1 (Chariot reagent, Active Motif Inc., CA) and HIV GP41 fragment (519-541), can be used.

Other carrier reagents include signal sequences, which have been used efficiently to target proteins to specific locations in both prokaryotic and eukaryotic cells, and a number of membrane-translocating peptides. Membrane-translocating peptides have been applied successfully to mediate membrane-translocation and the importation of a polpeptide, protein domain, full-length protein, or antibody into a cell using standard solution-based transfection protocols. The carrier reagent is a bioactive peptide or ligand that can specifically bind to and activate cell surface receptors. After binding to the cell surface receptors, the receptor and bound carrier-protein complex will undergo internalization, delivering ligand-protein complexes into cells. The proteins may be complexed with the ligand beforehand or in situ. The ligand can be complexed with the protein of interest or the protein to be introduced into cells by means of non-covalent interaction such as hydrophobic interaction or electrostatic interaction or both, or coupled covalently to the protein, or by means of a ligand-receptor binding interaction. For example, a carrier reagent can be modified with a ligand that can bind specifically to the protein of interest. To illustrate, a synthetic ligand termed "Streptaphage" has efficiently delivered streptavidin to mammalian cells by promoting non-covalent interactions with cholesterol and sphingolipid-rich lipid raft subdomains of cell plasma membranes (Hussey, S. L. & Peterson, B. R., J. Am. Chem. Soc., 124, 6265-6273 (2002)).

In another embodiment, the carrier reagent is a lipid liposome or the like that can complex with a protein of interest and promote the delivery of the protein into the cell. For example, the protein encapsulated in the formulation binds to the negatively vehicle for delivery (O. Zelphati et al., J. Bio. Chem., 276, 35103-19 (2001)). Products available commercially can be used, such as BioPORTER (Gene Therapy Systems), or ProVectin (Imgenex, San Diego, Calif.).

Protein delivery reagents (e.g., Chariot™ by Active Motif, or BioPORTER® by Gene Therapy Systems) can help save time by bypassing the traditional DNA transfection, transcription and protein translation processes associated with gene expression. Depending on the nature of the particular reagent employed, fusion proteins or chemical coupling in some embodiments would not be needed. The reagent forms a complex with the protein, stabilizes the macromolecule and protects it from degradation during delivery. Once internalized in a cell, the complex can dissociate, leaving the macromolecule biologically active and free to proceed to its target organelle.

Helper Reagents

The particular embodiments of the invention are described in terms of a helper reagent. In one embodiment, the helper reagent is a polymer such as DEAE-dextran, dextran, polylysine, and polyethylamine. In another embodiment, a helper reagent can also be a cell adherent-enhancing protein, such as fibronectin and gelatin. The helper reagent can be a sugar-based gelatin (e.g., polyethylene glycol) or a synthetic or chemical-based gelatin, such as acrylamide. In a further embodiment, the helper reagent can be a RGD peptide, such as Arg-Gly-Asp-Ser, Arg-Gly-Asp-Ser-Pro-Ala-Ser-Ser-Lys-Pro, and the like. Alternatively, the helper reagent can be a mixture of a hydrogel and a RGD peptide, and combination of any the aforementioned molecules. The use of helper reagents enhances the efficiency of protein delivery into the cells.

Substrates

The substrates used in the present invention for arrays comprise at least one surface on which a pattern of probe spots (protein-containing mixture microspots) may be affixed. The surface may be either solid or porous. Also, the surface may be either smooth and substantially planar, or have irregularities, such as depressions or elevations. The surface on which the pattern of spots is present can be modified with one or more different layers of compounds, which serve to change the surface-chemistry properties in a desirable fashion. For example, the surface may be coated with chemical molecules that can enhance the binding of the protein-containing mixture, while simultaneously still allowing the proteins to be transfected into cells, which are overlaid on top of the protein-containing mixture microspots. For instance, a coating of γ-aminopyropyl silane (GAPS) or polylysine may be applied to a glass surface.

The substrate may be fabricated from a ceramic, glass, metal, plastic, polymer or co-polymer, crystalline, or conductive material (e.g., indium tin oxide), or any combinations thereof; alternatively, the surface may have a coating of one of such materials on another. Such substrates include, but are not limited to, for example (semi) noble metals such as gold or silver; glass materials such as soda-lime glass, pyrex glass, vycor glass, quartz glass; metallic or non-metallic oxides; silicon, monoammonium phosphate, and other such crystalline materials; transition metals; plastics or polymers, including dendritic polymers, such as poly(vinyl chloride), poly (vinyl alcohol), poly(methyl methacrylate), poly(vinyl acetate-maleic anhydride), poly(dimethylsiloxane) monomethacrylate, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these, or the like.

The substrate may take a variety of configurations depending on the intended use of the array, ranging from simple to complex. For microarray uses, the substrate can be a slide or plate, such as of a rectangular or disc configuration. Alternatively, a standard, multiwell microplate can have spots deposited in each well. In many embodiments, the substrate will have a rectangular shape in cross-section with a length of from about 20-200 mm, and a width of from about 10-150 mm.

Particular embodiments of the surface include the bottom of a well in a single or multi-well microplate or strip-of-wells of any commercially available format (e.g., 6, 8, 12, 24, 48, 96, 192, 384, 576, etc.). Aside from a microplate, the substrate surface may be that of a microcolumn or micropillar device, such as described in U.S. Provisional Application No. 60/317,660, the content of which is incorporated herein in its entirety. Microcolumns can have a variety of shapes, such as a cube, cylinder, cone, frustoconical or polygonal body.

Preparation of the Arrays

Arrays for the present invention may be prepared using a multiplicity of micro-patterning techniques. In one embodiment, the tip of a mechanical projection or probe (also referred to as a "pin") is immersed into a solution of a protein-containing mixture. The tip is removed from the solution with an amount of solution adhered to the tip. The wetted tip makes contact with the surface of a substrate, thereby transferring the solution from the tip to the surface.

A "pin" as applied according to the present invention may be of any shape, size, and dimension. For example, the pin printing process may involve ring shaped pins, square pins, or point pins, etc. In another embodiment, the direct contact printing may involve single pin-printing or multiple pin-printing, that is, a single pin printing method involving a source plate or multiple pin-printing using a laid out array of multiple pins patterned in any format.

The printing apparatus may include a print head, plate, substrate handling unit, XY or XYZ positioning stage, environmental control, instrument control software, sample tracking software, etc. Such an apparatus may include, for example, a quill pin-printer available from Cartesian Technologies, Inc.

For a high-density array, a typographical probe array having a matrix of probes may be used to align and fit each probe from the matrix into a corresponding source well (e.g., a well of a microtiter plate).

A variety of other techniques may also be used to produce the array of protein-containing mixtures of the present invention. For example, arrays of the present invention can be produced using microstamping (U.S. Pat. No. 5,731,152), microcontact printing using PDMS stamps (Hovis 2000), capillary dispensing devices (U.S. Pat. No. 5,807,522) and micropipetting devices (U.S. Pat. No. 5,601,980). For radioactive assays using arrays of protein-containing mixtures, pipette-based liquid transfer techniques are preferred for fabricating the arrays because such techniques can give rise to spots of larger size with a range of several hundred microns to several millimeters.

Use of the Array

Once a substrate is prepared, bearing an array comprising a plurality of microspots of protein-containing mixtures, cells are plated or otherwise placed onto the substrate surface in sufficient density and under appropriate conditions for the introduction of the proteins into the cells. Clusters of live cells that have taken up a protein at each location, i.e., transfected with the proteins, will cover the array. As mentioned before, the present invention can be applied to a variety of cells, including eukaryotic cells, such as mammalian cells (e.g., human, monkey, mouse, etc.), bacterial, insect or plant cells. Preferably, the cells (in a serum or serum-free medium) are plated on top of the dried protein-containing spots at high density (e.g., $0.5-1\times10^5/cm^2$), in order to increase the likelihood that reverse transfection occurs. Alternatively, the density of cells may vary from about $0.3\times10^4/cm^2$ to about $5\times10^5/cm^2$; or, in other embodiments, from about $2\times10^5/cm^2$ to about $3\times10^5/cm^2$; or, from about $0.5\times10^4/cm^2$ to about $2\times10^5/cm^2$.

Transfected cell microarrays can be of broad utility for high-throughput study of biological function of proteins, as well as screening compounds that affect the specific function of the proteins in a cell. Particularly, transfected cell arrays are useful for probing single transduction pathways, blocking transcription factors, for conducting detailed structure-function analysis of integrin and other receptors' cytoplasmic domains, and for drug discovery. A variety of techniques may be employed to detect the effects of the protein of interest on recipient cells (i.e., cells that have been delivered of the protein). These techniques may include, for instance, immunofluorescence, in which a fluorescently-labeled antibody that binds a protein of interest is used to determine if the protein is present in cells.

Moreover, a microplate-based reverse protein delivery technique can be employed for cell culture and localized cell transfection. A microplate may be pre-coated with protein-containing mixtures, or a certain amount of a solution containing a protein of interest pre-complexed with a carrier reagent can be deposited onto the bottoms of each single wells, allowing the mixture dry and affixed on the surface of each well.

Another application of the present method targets the use of "protein-transfection" to express proteins in primary cell lines, which are difficult to transfect using classical DNA-based techniques. According to this embodiment, DNA-constructs expressing the protein of interest are first transfected or otherwise introduced into a population of relatively "easy to transfect" cells, such as, but not limited to HeLa, 3T3, HEK 293, COS. Afterwards, this first population of cells is desposited onto a surface. Using an immobilized cell has an advantage of amplifying in-vivo protein production before deliver into primary cells. After either in situ lysis of these cells and local capture of these proteins, such as using a tag, or in situ excretion of the expressed protein of interest onto the surface, primary cells can be added and are transfected by the fusion proteins in a local manner. Then, a second population of primary cells is deposited over the proteins present on the surface, and the proteins are delivered into the primary cells. Alternatively, the method can work with arrays of fusion proteins, as described above, are delivered into relatively "easy to transfect" cells. The result is a surface or an array of primary cells, each expressing a different fusion protein.

The pertinent content of each of the articles and publications made reference to in the present specification is incorporated herein by reference.

Example

The following empirical example further describes and illustrates the present invention. The particular example, described in terms of proteins, is not limiting of the present invention. It is understood that any suitable amino acid sequence, including peptides, proteins, antibodies, or protein-nucleic acid conjugates, is encompassed by the present invention. The proteins will have an effect on a cellular function or interact with a cellular component.

Example

Reverse Delivery of β-Galactosidase into Cells

Materials

The materials used included: β-galactosidase (grade VIII, purified from *E. Coli*), RGD peptides gly-arg-gly-asp-ser, and gly-arg-gly-asp-ser-pro-lys), dextran (M.W. 45000 Da), and DEAE-detran (M.W. 40000 Da) (Sigma Chemical (St.

Louis, Mo.)); Chariot (Pep-1) (Active Motif Inc, Carlsbad Calif.); and HIV GP-41 fragment (519-541) (Bachem (King of Prussia, Pa.)); and Gamma-Amino Propyl Silane (GAPS) slides were obtained from Corning Inc (catalog #2550) (Corning, N.Y.). Cell culture media was obtained from Gibco. A β-galactosidase staining kit was obtained from Qiagen. Other chemicals were from Sigma.

Method

Stock Solution Preparations

In 10 mM PBS buffer (pH 7.4), β-galactosidase was dissolved to a concentration of 0.25 mg/ml, and stored at 4° C. Translocation peptides (i.e., carrier peptide), Chariot or GP41 fragment, were dissolved in 60% DMSO to a concentration of 2 mg/ml, and stored at −20° C. before use. Dextran or DEAE-dextran was dissolved into $ddH_2O$ to give a concentration of 2%, and stored at 4° C. RGD peptides was dissolved in PBS buffer to give a concentration of 1 mg/ml, and stored at −20° C. before use. Dextran, DEAE-dextran and RGD peptides were used as a helper reagent to enhance the delivery efficiencies.

Diluting and Mixing

The β-galactosidase stocking solution was diluted into PBS buffer to give final protein concentration of 0.1 mg/ml. Peptide stock solution was diluted into PBS buffer to give a final concentration of 0.4 mg/ml, and subject to sonication to avoid self-aggregation. Two diluted solutions were gently mixed together using equal volume. Helper reagent can be also added into the mixture (optimized concentrations for these helper reagent are 1 mg/ml for dextran and DEAE-dextran, 0.1 mg/ml for RGD peptides). The resulted mixture was incubated at room temperature for about 30 minutes to one hour.

Spotting

On a slide surface coated with γ-amino-propylsilane (Corning Inc., Corning, N.Y.), 20 spots in four separated grids, each having 5 replicated spots within a single grid, was made using 5 μl of the mixture solution, and dried at room temperature for one hour.

Storage

The slides bearing protein-containing spots, in some cases, were stored at 4° C. in nitrogen for several days to several weeks, with no observable loss of protein transfection efficiencies or functionality of the proteins inside the transfected cells.

Cell Type and Culture Conditions

Human Embryonic Kidney (HEK) 293T cells and CHO cells cultured in Iscove's Modified Dulbecco's Medium (IMDM) supplemented with 10% fetal bovine serum.

Cell Culture and Transfection

In a tissue culture hood, a suspension containing about $0.5-2 \times 10^5$ cells (CHO or HEK) was plated or otherwise deposited on top of each grid containing separated protein spots. The cell suspension either contained serum or was serum-free. For transfection, the cells attached and grew for 3 hours under 5% $CO_2$ and 95% humidity.

Fixation of Cells

After culturing, the slides were twice rinsed very gently with PBS buffer, and then fixed in 4% formaldehyde/PBS solution for 3 minutes, and again rinsed twice with PBS buffer.

X-Gal Staining

Following the standard protocol recommended by the supplier, reagent solution from a β-galactosidase staining kit (Invitrogen) were added to the fixed cells, and incubated with the cells for 30 minutes at 37° C.

Cell Examination

Using a light microscope, the percentage of cells stained blue color was counted to calculate the protein transfection efficiencies with β-galactosidase. The stained cells could be stored after disposing of the staining solution and overlaying with 70% glycerol.

Figure 3:
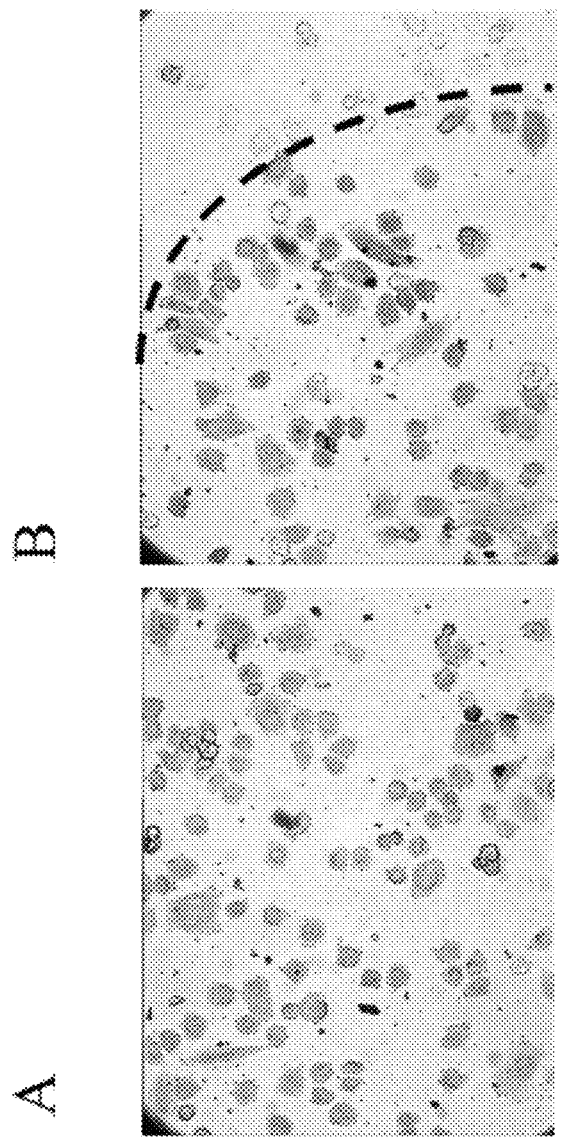
FIGS. 3A and B are light microscopic images of CHO cells cultured on top of a dried, protein-containing spot on a GAPS-coated glass surface after being fixed and stained. The protein mixture contained beta-galactosidase ($\beta$-gal), a carrier (GP 41 peptide (HIV gp41 fragment 519-541)), and a helper reagent (DEAE-dextran). Cells that have been stained blue (darker) with x-gal solution are ones into which the proteins on the surface have successfully transfected. The blue color indicates that the $\beta$-gal protein on the surface entered the cells and is still fully functional. The dot line in the image of FIG. 3B, on the right, delineates the edge of the spot.

As illustrated in FIG. 3, certain percentages of the cells on the top of the protein-containing spots turned blue after X-gal staining, suggesting that these proteins on the surface entered the cells, and these proteins are still fully functional inside the cells. As evidenced by the appearance of blue color after X-gal staining, the cells of both cell lines become transfected when deposited on top of the mixture spots containing beta-gal and delivery vehicle (VP41 fragment). The reverse delivery process took a relatively short time. Reaction typically takes place within 3 hours. Protein delivery into the cells appears to be highly efficient. Cells plated on the protein-mixture spots for as short a time as only 3 hours become transfected. Although not required to use of serum-free medium, the use of serum-free medium does improve the transfection efficiency of the reverse protein delivery process. The presence of DEAE-dextran, dextran, RGD peptide (Gly-Arg-Gly-Asp-Ser-Pro-Lys) or the combination of these reagents also improves the efficiency. In some experiments the cells attached to the mixture spots were trypsinized following X-gal staining and replated in a microplate well. Significantly, the blue x-gal color remained within the cells, strongly suggesting that that the blue color is indeed intracellular, derived from the fully-functional β-gal delivered into the cells.

The present invention has been described in detail by way of examples. Persons skilled in the art, however, may appreciate that modifications and variations may be made to the present method and device without departing from the scope of the invention, as defined by the appended claims and their equivalents.

We claim:

1. A method of making an apparatus for performing surface-mediated protein delivery into living cells comprising:
   providing a protein-containing mixture comprising a protein-of-interest, a carrier reagent and a helper reagent, wherein the carrier reagent is a peptide containing a protein transduction domain (PTD) and wherein the helper reagent is DEAE-dextran, dextran or a peptide containing an RGD sequence;
   spotting said protein-containing mixture having said carrier and said helper reagent onto a surface at defined and discrete locations;
   drying—the protein-containing mixture having said carrier and said helper reagent on the surface.

2. The method according to claim 1, wherein said protein of interest is selected from the group consisting of a bioactive peptide, intracellular protein, enzyme, cell surface protein, toxin protein, antibody, antibody-nucleic acid conjugate, protein-nucleic acid conjugate, peptide-nucleic acid conjugate, protein polymer conjugate, conjugate between a protein-organic chemical entity or protein inorganic chemical entity, multi-protein complexes, any amino-acid containing moiety and combinations thereof.

3. The method according to claim 1, wherein said protein of interest comprises a fusion protein that contains a translocation domain and a protein domain of interest.

4. The method according to claim 1, wherein the carrier reagent comprises a naturally occurring or synthetic translocation peptide, or a liposome.

5. The method according to claim 1, wherein said helper reagent is a RGD peptide selected from the group consisting of: Arg-Gly-Asp-Ser (SEQ ID NO: 2), Arg-Gly-Asp-Ser-Pro-Ala-Ser-Ser-Lys-Pro (SEQ ID NO: 3).

6. The method according to claim 1, wherein said surface is that of a microtiter plate well-bottom, a microcolumn, a slide, a strip, a bead, a particle, or nanoparticle.

7. The method according to claim 1, wherein said defined locations comprise an array of microspots on said substrate surface.

8. The method according to claim 7, wherein said defined locations each contains a different protein-of-interest.

9. The method according to claim 7, wherein each different protein-of-interest is included on more than one separate microspot on the array.

10. The method according to claim 7, wherein said microspots on the array comprises the same protein-of-interest but with different point mutations.

11. The method according to claim 9, wherein the different proteins-of-interest are functionally related.

12. The method according to claim 7, wherein said array form a thematic microarray.

13. A high-throughput biological analysis device comprising an apparatus for performing surface-mediated protein delivery made according to the method of claim 1.

14. The device according to claim 13, wherein said surface comprises a microtiter plate well-bottom, a microcolumn, a slide, a strip.

15. The device according to claim 13, wherein said surface comprises ceramic, glass, metal, polymer or co-polymer, crystalline, or conductive material, or any combinations thereof.

16. The device according to claim 13, wherein said surface comprises a coating of any one of said materials on another.

17. The device according to claim 13, wherein said defined locations comprise an array of microspots on said surface.

18. The device according to claim 17, wherein said defined locations each comprise a different protein-of-interest.

19. The device according to claim 17, wherein at least two of the microspots comprise different proteins-of-interest.

20. The device according to claim 17, wherein said microspots on the array comprises proteins-of-interest different point mutations.

21. The device according to claim 17, comprising proteins-of-interest that are functionally related.

22. The device according to claim 17, wherein said array is a thematic microarray.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Gly Arg Gly Asp Ser Pro Lys
1               5
```

```
<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Gly Arg Gly Asp Ser
1               5
```